United States Patent [19]

Renner et al.

[11] 4,031,130
[45] June 21, 1977

[54] ALIPHATIC β-KETO ESTERS

[75] Inventors: Günter Renner; Immo Boie; Quirin Scheben, all of Cologne, Germany

[73] Assignee: AGFA-Gevaert, A.G., Leverkusen, Germany

[22] Filed: Mar. 11, 1975

[21] Appl. No.: 557,268

[30] Foreign Application Priority Data

Mar. 16, 1974 Germany .......................... 2412784

[52] U.S. Cl. .............................. 260/468 K; 96/89; 260/483; 260/559 B
[51] Int. Cl.² ......................................... C07C 69/74
[58] Field of Search ..................... 260/468 K, 483

[56] References Cited

OTHER PUBLICATIONS

Fieser et al., Reagents for Organic Synthesis, vol. 3, 149–150, (1970).

House, Modern Synthetic Reaction, 744–754, (1972).
Normant, Angew. Chem. Int. 6, 1056, 1061, (1967).
Krapcho et al., Org. Synthesis, 47, 20 (1967).

*Primary Examiner*—Robert Gerstl
*Attorney, Agent, or Firm*—Connolly and Hutz

[57] ABSTRACT

A process for the production of aliphatic β-keto esters by reacting a dialkyl ketone with a dialkylcarbonate in the presence of an at least equivalent quantity of a basic condensation agent based on the dialkyl ketone at a reaction temperature of 20° to 80° C and the reaction product is subsequently converted by acidification into the β-keto ester. By carrying out the condensation reaction in the presence of hexamethylphosphoric acid triamide as solvent advantageously higher yields of 20 to 50 % can be obtained by the inventive process of compared to conventional processes.

11 Claims, No Drawings

ALIPHATIC β-KETO ESTERS

This invention relates to a process for the production of aliphatic β-keto esters, more especially sterically hindered aliphatic β-keto esters, in excellent yields. The synthesis of β-keto esters is known and is described, for example as Claisen's condensation, in numerous text books and publications. In general, carboxylic acid esters are reacted as the carbonyl component with C-H-acid carboxylic acid esters to form β-keto carboxylic acid esters in an inert solvent in the presence of at least equimolar quantities of basic catalysts such as, for example sodium hydride, sodium amide, triphenyl methyl sodium and alkali metal alcoholates, as condensation agents. Mixed ester condensations are generally only carried out with formic acid esters as the carbonyl component because it is only in this way that it is possible to obtain clearly defined reaction products.

Examples of condensation reactions of this kind are described in articles in "J. Amer. Chem. Soc." 72, 1352 (1950); 66, 862 (1944); 66, 1768 (1944); 63, 2252 (1941); 63, 3156 (1941), and in U.S. Pat. Nos. 2,407,942 and 2,367,632.

Unfortunately, the yields obtained from these reactions, in the case of sterically hindered aliphatic β-keto esters such as, for example, pivaloyl acetic esters, only amount to around 40%, even in cases where strongly basic catalysts such as sodium hydride, sodium amide in liquid ammonia or triphenyl methyl sodium, are used. Hitherto, condensation agents which are easier to handle in preparative terms, such as alkali metal alcoholates, have only produced very poor yields, for example in the case of pivaloyl acetic ester, because the β-keto ester formed during the condensation reaction presumably has a higher level of reactivity than the starting compound to be reacted, which can give rise to numerous secondary reactions during the condensation reaction.

Accordingly, it has already been proposed to produce β-keto esters by reacting aceto acetic esters with acid chlorides in the presence of magnesium alcoholates, followed by hydrolytic dissociation of the reaction product to form the required β-keto ester, as described in British patent specification No. 1,000,709. Unfortunately, this method is also attended by numerous difficulties in practice so that, for example in the case of pivaloyl acetic ester, the yields obtained generally amount to no more than 40%. Since for example the level of activity of commerical-grade magnesium alcoholate is not sufficient, the magnesium alcoholate required for the reaction always had to be freshly prepared, which can give rise to considerable difficulties in large-scale working. In addition, the pivalic acid chloride required for the reaction is difficult to process on account of its pungency, and the temperature at which the reaction is carried out is difficult to control, even in cases where freshly prepared magnesium alcoholate is used. Furthermore, alkaline dissociation of the β-diketo carboxylic acid ester formed as intermediate results in the formation not only of pivaloyl acetic ester but also, through a secondary reaction, in the formation of aceto-acetic ester and pivalic acid. Accordingly, the pivaloyl acetic ester thus formed can only be obtained with difficulty in pure form from the mixture of β-keto esters by distillation.

Accordingly, there is in practice a need to find a preparatively simple process by which it is possible to produce aliphatic β-keto esters, more especially sterically hindered β-keto esters, in higher yields and in greater purity than is possible by conventional processes.

It has now been found that aliphatic β-keto esters, more especially sterically hindered aliphatic β-keto esters, can be obtained in improved yields by reacting dialkyl ketones with dialkyl carbonates and at least equimolar quantities of a basic condensation agent in known manner, using hexamethyl phosphoric acid triamide as solvent.

It has been found that, in cases where hexamethyl phosphoric acid triamide is used as solvent, it is possible to obtain an increase in yield of from 20 to 50% by comparison with conventional reactions.

Accordingly, the invention relates to a process for the production of aliphatic β-keto esters, in which dialkyl ketones are introduced slowly into a solution of, preferably, excess dialkyl carbonate and at least an equivalent quantity of a basic condensation agent based on the dialkyl ketone, in hexamethyl phosphoric acid triamide at reaction temperatures in the range of from 20° to 80° C, and the reaction product formed subsequently coverted by acidification into the β-keto ester.

Basic condensation agents suitable for use according to the invention include alkali or alkaline earth metal alcoholates such as sodium methylate, sodium ethylate, potassium ethylate, potassium-t-butylate or magnesium ethylate, sodium amide, sodium hydride and triphenyl methyl sodium. Of the alcoholates, potassium-t-butylate is preferred.

The quantity in which the basic condensation agent is used should be at least equivalent to the quantity in which the dialkyl ketone is used. In cases where the alcoholates are used as condensation agents, it is preferred to use an excess of approximately 5%, although this may even be higher, especially in the case of potassium-t-butylate. In cases where sodium hydride is used as the condensation agent, it is preferred to use more than 2 mols of sodium hydride per mol of dialkyl ketone used.

Dialkyl carbonates suitable for use in accordance with the invention are compounds corresponding to the following general formula:

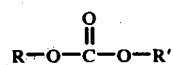

$$R-O-C(=O)-O-R' \quad \text{I}$$

in which the radicals R and R' may be the same or different and represent alkyl radicals preferably with 1 to 4 carbon atoms, such as propyl, isopropyl, methyl and, in particular, ethyl. The preferred dialkyl carbonate is diethyl carbonate.

The quantity in which the dialkyl carbonate is used should be at least equivalent to the quantity in which the dialkyl ketone is used. However, the dialkyl carbonate is preferably used in a 2- to 10-molar excess.

The hexamethyl phosphoric acid triamide used as solvent should be employed in such a quantity that it accelerates the reaction to a sufficient extent. It is preferred to use at least 0.1 mol of hexamethyl phosphoric acid triamide per mol of dialkyl ketone to be reacted as solvent.

The hexamethyl phosphoric acid triamide may of course be used in larger quantities. If desired, the excess hexamethyl phosphoric acid triamide can be recovered from the aqueous phase by extraction with chloroform after the reaction mixture has been treated in the usual way on completion of the reaction, and reused.

The process according to the invention is suitable for the reaction of standard, known alkyl ketones and is particularly suitable for the reaction of ketones of the kind which can only be reacted with dialkyl carbonates with difficulty or in poor yields by conventional methods.

In principle, methyl alkyl ketones or methyl alkyl ketones which are monosubstituted, especially monoalkylated, on the methyl group, are suitable for use as the dialkyl ketones which may be reacted in accordance with the invention to form β-keto esters, and can be reacted in high yields.

Naturally, monoalkylated methyl alkyl ketones also include ketones of the kind whose alkyl substituents together form of multimembered aliphatic ring.

It is in practice of particular advantage to react methyl alkyl ketones substituted or unsubstituted on the methyl group in accordance with the invention to form sterically hindered β-keto esters which, in the following, is intended to signify that the reactivity of the ketone used for the reaction is influenced by substituent influences so that the ketones in question could only be reacted to form β-keto esters in moderate yields by conventional methods.

Accordingly, dialkyl ketones suitable for use in accordance with the invention are compounds corresponding to the following general formula:

in which

R$^1$ represents an alkyl radical preferably with 1 to 18 carbon atoms, such as methyl, ethyl, propyl, butyl, dodecyl, octadecyl, more especially isopropyl or t-butyl, and R$^2$ represents hydrogen or an alkyl group with 1 to 4 carbon atoms, more especially methyl or ethyl, in addition to which R$^1$ and R$^2$ may together represent the atoms required to complete a multi-membered aliphatic ring, more especially 5- to 7-membered aliphatic ring, such as a cyclopentanone, cyclohexanone or cycloheptanone ring.

Examples of dialkyl ketones which can be reacted in accordance with the invention to form high yields of β-keto esters, are pinacolone, diethyl ketone, methyl isopropyl detone and cyclohexanone.

Accordingly, the process according to the invention is particularly suitable for the production of pivaloyl acetic esters which are acquiring increasing significance in practice for the preparation of pivaloyl yellow couplers for photographic purposes. It is of advantage in the process according to the invention to avoid an excess of dialkyl ketone in the reaction mixture consisting of the hexamethyl phosphoric acid triamide, the dialkyl carbonate and the basic condensation agent. This can with advantage be achieved by adding the dialkyl ketone slowly and uniformly to the reaction mixture, so that there is only ever a small quantity of unreacted ketone present in the reaction mixture. The solvent, hexamethyl phosphoric acid triamide, can with advantage be diluted by the addition of another inert organic solvent. The preferred, additional solvent is the dialkyl carbonate used for the reaction. Benzene, toluene and xylene are also suitable. The dialkyl ketone can be added to the reaction mixture either directly or in solution in an inert solvent. In cases where alcoholates are used as the condensation agent, it is of advantage of the particular alcohol formed in the reaction mixture to be removed during the reaction by simultaneous distillation, and for its concentration to be kept as low as possible. Ideally, the alcohol should actually be removed from the reaction mixture at the moment it is formed. In general, the reaction is carried out by using the alcoholates corresponding to the dialkyl carbonate. However, it is preferred for example, especially where diethyl carbonate is used, to prepared the sodium ethylate in situ by reacting sodium metal with diethyl carbonate and directly using it for the reaction. As already mentioned, the reaction temperature is in the range from 20° to 80° C, and the fractions of alcohol formed during the reaction are distilled off through a column, optionally under a light vacuum of 100 to 500 Torr. Where it is used for example in molar quantities, the ketone is continuously added over a period of preferably more than 2 hours.

In the context of the invention, the term "continuous addition", apart from continuous addition in its strict sense, is also meant to include addition in small quantities and at brief time intervals as obtained, for example, by dropwise addition or with peristaltic pumps.

In cases where sodium hydride is used as the condensation agent, about 1/10 of the ketone to be used is initially added to the solvent mixture of hexamethyl phosphoric acid triamide and, optionally, another inert solvent, and to the dialkyl carbonate and condensation agent, and the reaction mixture briefly heated to a temperature of from 50° to 80° C. After the reaction has started, the reaction mixture is cooled to around 40° C and the rest of the ketone is added slowly and continuously as described above. As already mentioned, the reaction temperature in the process according to the invention should be kept in the range from 20° to 80° C.

On completion of the reaction, the alkali salts of the β-keto esters are directly obtained and may either be immediately further reacted or converted in the usual way by acidification (aqueous HCl—, aqueous H$_2$SO$_4$ or acetic acid) into the free β-keto ester, the pH-value being adjusted to about 6. Following extraction of the reaction products with an organic solvent, for example ethyl acetate or toluene, the esters are purified preferably by distillation.

Where chloroform is used, the solvent, hexamethyl phosphoric acid triamide, is enriched in the organic phase which can be removed during the subsequent distillation stage. However, since the β-keto esters formed are used as intermediate products for the production of yellow couplers, the solvent does not have to be removed because it does not interfere with the subsequent reaction.

Where the process according to the invention is carried out with sodium amide as the condensation agent, a substantially quantitative conversion of the dialkyl ketone and a yield of corresponding pure β-keto ester of more than 90% in the case of pivaloyl acetic ester are obtained. Where sodium hydride is used as the condensation agent, it was possible to obtain yields of 90%, whilst the yields obtained in the case of potassium-tert.-butylate were still in excess of 60% and, in the case of sodium ethylate, of the order of 30%. Hitherto, it had not been possible to obtain yields of this order in corresponding reactions carried out by conventional methods where the yields have always been some 20 to 50% lower than those quoted above.

EXAMPLE 1

Preparation of Pivaloyl Acetic Esters 1. 23 g of sodium were slowly introduced in small portions into 840 cc of diethyl carbonate, followed by heating to boiling point. After a reaction time of 15 minutes, all of the sodium had been converted into sodium ethylate. The reaction solution was then cooled to 60° C and 500 cc of benzene and 200 cc of hexamethyl phosphoric acid triamide were added. A solution of 100 g of pinacolone in 250 cc of benzene was then added dropwise over a period of 3 hours at a temperature of 50° to 60° C and under a vacuum of 180 Torr. and benzene and ethanol simultaneously distilled off. Another 500 cc of benzene were then added and distillation continued. The total reaction time was 9 hours.

After cooling, the reaction mixture was poured into water, acidified and after extraction with ethyl acetate or toluene the solvent was distilled off. The residue containing the pivaloyl acetic ester was purified by distillation. The yield was 30 % of pivaloyl acetic acid ethyl ester.

2. A solution of 100 g of pinacolone in 500 cc of benzene was added dropwise over a period of 4 hours at 50° C/150 Torr to a solution of 500 cc of benzene, 900 cc of diethyl carbonate, 125 g of potassium-tert.-butylate and 200 cc of hexamethyl phosphoric acid triamide, and benzene and ethanol slowly distilled off. After the ketone had been added, another 500 cc of benzene were added dropwise. The total reaction time was 9 hours. The reaction mixture was then treated and distilled in the same way as described in 1 above. The yield was 54% of pivaloyl acetic acid ethyl ester.

3. 250 g of potassium-tert.-butylate were suspended in a solution of 480 cc of diethyl carbonate and 100 cc of hexamethyl phosphoric acid triamide, followed by the gradual dropwise addition of 100 g pinacolone at 45° C/normal pressure. On completion of the addition, the mixture was stirred for 1 hour at 45° C and, after cooling, alcohol, water and finally hydrochloric acid carefully added one after the other to the reaction mixture. The reaction mixture was then treated and purified in the same way as described in 1 above. The yield was 67% of pivaloyl acetic acid ethyl ester.

4. 325 g of sodium hydride (80% solution in paraffin oil) were suspended in 2500 cc of diethyl carbonate and 500 cc of hexamethyl phosphoric acid triamide, 500 g of pinacolone (92%) were then slowly added dropwise at 45° to 50° C. and, on completion of the addition the reaction mixture was treated as described in 3 above. The yield was 91% of pivaloyl acetic acid ethyl ester.

5. The procedure was as in test 4 above, except that 60 g of sodium hydride in 850 cc of diethyl carbonate, 500 cc of benzene and 200 ml of hexamethyl phosphoric acid triamide, and 100 g of pinacolone (92%) were used, and the reaction temperature was kept at 35° C. The yield was 78%.

6. The procedure was as in test 5 above, except that no benzene was used and the reaction temperature was kept at 20° to 30° C. The yield was 72%.

7. The procedure was as in test 4 above, except that 65 g of sodium hydride in 480 cc of diethyl carbonate and 100 cc of hexamethyl phosphoric acid triamide, and 100 g of pinacolone (92%) were used and the reaction temperature was kept at 65° C. The yield was 65%.

8. The procedure was as in test 4 above, except that 390 g of sodium hydride in 2900 cc of diethyl carbonate and 300 ml of hexamethyl phosphoric acid triamide, and 600 g of pinacolone (92%) were used. The yield was 87%.

9. 60 g of sodium hydride were suspended in 450 cc of dimethyl carbonate and 100 cc of hexamethyl phosphoric acid triamide. 100 g of pinacolone (92%) were added slowly at 45° C and on completion of the addition, the reaction mixture was processed as described in 3 above. The yield was 83.5% of pivaloyl acetic acid methyl ester.

10. The procedure was as in test 9 above, except that 325 g of sodium hydride in 1800 cc of dimethyl carbonate and 200 cc of hexamethyl phosphoric acid triamide, and 500 g of pinacolone (92%) were used. The yield was 82%. The pivaloyl acetic esters obtained according to the methods 1 - 10 above can be converted by reacting equimolar amounts of pivaloyl acetic esters and an substituted aniline such as e.g. 2-chlor-5-[2',4'-di-t-amylphenoxybutylamido]aniline in an inert organic solvent such as xylol or benzene to a pivaloylacetic acid anilide coupler compounds e.g. of the formula

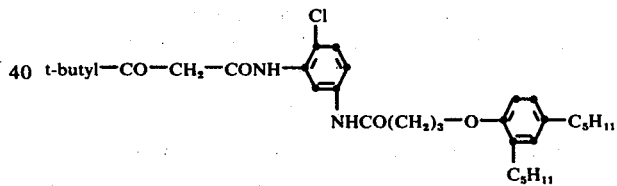

The pivaloylacetic acid anilide coupler compounds can be used in known manners for the preparation of photographic images in color photographic materials e.g. as following:

2 mmol of the above mentioned coupler are solved in 3 ml. of acetic acid ethylester and after the addition of 1 g of dibutylphthalate are emulsified by 60° C to 20 ml of a 5% gelatin solution in known manner. The emulsion contains 0,10 g sodium salt of dodecylsulfonic acid. The emulsion was then added to 85 g of a 7,5 % gelatin solution which contains in dispersed form 1,93 g of silver bromide and diluted with water to read to viscosity which is necessary for casting the emulsion. The emulsion is then cast onto a transparent support of cellulose triacetat and dried.

The photographic material is then developed after imagewise exposure behind a grey step wedge in a color developer containing N,N-diethyl-p-phenylene-diamine as color developer substance. After normal bleaching and fixing a yellow step wedge was obtained having an absorption maximum of 436 nm.

EXAMPLE 2

Preparation of 3-Keto-4-Methyl Valeric Acid Ethyl Ester 10 g of methyl isopropyl ketone were added to a solution of 400 cc of benzene, 850 cc of diethyl carbonate, 200 cc of hexamethyl phosphoric acid triamide and 60 g of sodium hydride (80% in paraffin oil), and the reaction mixture was heated to 70° to 80° C. After the reaction had started, the reaction mixture was cooled to approximately 30° C, and a solution of 76 g of methyl isopropyl ketone in 200 cc of benzene was added dropwise over a period of 2 hours at that temperature. After the reaction mixture had stood overnight, methanol was carefully added to it with cooling, followed by acidification with aqueous hydrochloric acid. The reaction mixture was then treated as described in Example 1.1. The yield was 81% of 3-keto-4-methyl valeric acid ethyl ester.

The compound of Example 2 can be converted with anilines to α-methyl-propionylacetanilides e.g. according to the method described above which can be used in photographic materials as so called white couplers. The α-alkyl substituted β-keto-carbonic-acid-anilides react with oxidized color developer substances of the p-phenylene diamine type to form compounds which are not colored. Thus they are used in color photographic materials in photographic layers for diminishing the color fog produced by a certain amount of oxidation products of color developer substances which is present even in unexposed areas of the photographic image due to diffusion processes.

EXAMPLE 3

Preparation of 2-methyl-3-keto valeric acid ethyl ester

The procedure was as in Example 2, except that diethyl ketone was used instead of methyl isopropyl ketone. The yield was 72% of 2-methyl-3-keto valeric acid ethyl ester.

EXAMPLE 4

Preparation of 2-carbethoxy cyclohexanone

The procedure was as in Example 2, except that cyclohexanone was used instead of methyl isopropyl ketone. The yield was 85% of 2-carbethoxy cyclohexanone.

The aforementioned compound can be converted by reaction with anilines into valuable white couplers suitable for use in color photographic materials.

We claim:

1. In a process for the production of an aliphatic β-keto ester by gradually adding a dialkyl ketone selected from the group consisting of pinacolone and methyl isopropyl ketone into a solution of dialkyl carbonate and a basic condensation agent which is capable of catalysing the ketone condensation reaction, said condensation agent being in a molar ratio of 1:1 or more based on the ketone, whereby said condensation reaction mixture is heated to a temperature of from 20° to 80° C until a reaction product is obtained and subsequently the reaction product obtained is acidified to produce the aliphatic β-ketoester, the improvement according to which the condensation reaction is carried out in the presence of at least 0.1 mol of hexamethyl phosphoric acid triamide per mol of the said dialkyl ketone in the condensation reaction mixture.

2. A process of claim 1 wherein the dialkyl carbonate used is of the formula

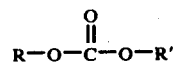

$$R-O-\overset{O}{\underset{\|}{C}}-O-R'$$

wherein
R and R' represent alkyl groups of from 1 to 4 carbon atoms.

3. A process of claim 1, wherein the dialkylketone is introduced into a molar solution of excess dialkylcarbonate based on the ketone.

4. A process of claim 1 wherein the basic condensation agent is selected from the group consisting of alkali and alkaline earth metal alcoholate, sodium amide, sodium hydride and triphenyl methyl sodium.

5. A process of claim 4 wherein the basic condensation agent is sodium methylate, sodium ethylate, potassium ethylate, potassium-t-butylate or magnesium ethylate.

6. A process of claim 1 wherein as basic condensation agent an alkali or alkaline earth metal alcoholate in an excess of 5 % based on the dialkylketone is used.

7. A process of claim 1 wherein as basic condensation agent sodium hydride in an amount of 2 mols per mol of dialkylketone is used.

8. A process of claim 2 wherein in the formula of the dialkylcarbonate R and/or R' represent propyl, isopropyl, methyl and/or ethyl groups.

9. A process of claim 1 wherein the dialkylcarbonate used is diethylcarbonate.

10. A process of claim 1 wherein the hexamethyl phosphoric acid triamide used is diluted with an inert organic solvent.

11. A process of claim 10 wherein the inert solvent used is selected from the group consisting of benzene toluene or xylene.